United States Patent
Nhan et al.

(10) Patent No.: US 9,138,354 B2
(45) Date of Patent: Sep. 22, 2015

(54) ATTACHMENT FOR A CONDUCTORLESS WETNESS DETECTOR FOR AN ABSORBENT ARTICLE

(71) Applicant: Kimberly-Clark Wordwide, Inc., Neenah, WI (US)

(72) Inventors: Davis-Dang Hoang Nhan, Appleton, WI (US); Sudhanshu Gakhar, Neenah, WI (US); Kristen Alene Decker, Neenah, WI (US); Brent Charles Otis, New London, WI (US); Paulin Pawar, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 284 days.

(21) Appl. No.: 13/727,844

(22) Filed: Dec. 27, 2012

(65) Prior Publication Data

US 2014/0188063 A1    Jul. 3, 2014

(51) Int. Cl.
  *G08B 21/00* (2006.01)
  *A61F 13/00* (2006.01)
  *A61F 13/42* (2006.01)

(52) U.S. Cl.
  CPC .......... *A61F 13/00055* (2013.01); *A61F 13/42* (2013.01)

(58) Field of Classification Search
  CPC ........................... A61F 13/00055; A61F 13/42
  USPC .................. 340/604, 573.1, 573.5, 603, 540; 604/361, 358, 385.03
  See application file for complete search history.

(56) References Cited

U.S. PATENT DOCUMENTS

| | | | |
|---|---|---|---|
| 4,106,001 A | 8/1978 | Mahoney | |
| 4,754,264 A | 6/1988 | Okada et al. | |
| 4,834,733 A * | 5/1989 | Huntoon et al. | 604/361 |
| 5,266,928 A | 11/1993 | Johnson | |
| 5,392,032 A | 2/1995 | Kline et al. | |
| 5,469,145 A | 11/1995 | Johnson | |
| 5,568,128 A | 10/1996 | Nair | |
| 5,722,968 A * | 3/1998 | Datta et al. | 604/391 |
| 5,838,240 A | 11/1998 | Johnson | |
| 5,902,296 A | 5/1999 | Fluyeras | |
| 6,097,297 A | 8/2000 | Fard | |
| 6,200,250 B1 | 3/2001 | Janszen | |
| 6,246,330 B1 | 6/2001 | Nielsen | |

(Continued)

FOREIGN PATENT DOCUMENTS

| | | |
|---|---|---|
| EP | 0 810 847 B1 | 8/2000 |
| JP | 2011-022121 A | 2/2011 |
| WO | WO 2005/067840 A1 | 7/2005 |

*Primary Examiner* — Daniel Previl
(74) *Attorney, Agent, or Firm* — Kimberly-Clark Worldwide, Inc.

(57) ABSTRACT

A wetness sensing system for use with an absorbent article includes a holding fixture adapted to be attached to the outer surface of the absorbent article by a consumer, the holding fixture including a first attachment arm having an article-facing side including a first attachment material affixed thereto, and a sensor band including a sensor and having an article-facing side including a second attachment material affixed thereto, wherein the second attachment material has an area and is in a proportion of the area to the weight of the system, and wherein the sensor band has a bending stiffness of less than 30 gf cm^2/cm. The system also includes a signaling device coupled to the holding fixture and in electrical communication with the sensor, wherein the system is adapted to sense wetness within the article without the use of conductors within the absorbent article.

20 Claims, 2 Drawing Sheets

(56) References Cited

U.S. PATENT DOCUMENTS

| | | |
|---|---|---|
| 7,977,529 B2 | 7/2011 | Bergman et al. |
| 8,274,393 B2 | 9/2012 | Ales et al. |
| 2004/0207530 A1 | 10/2004 | Nielsen |
| 2004/0220538 A1 | 11/2004 | Panopoulos |
| 2004/0230172 A1 | 11/2004 | Shapira |
| 2006/0244614 A1* | 11/2006 | Long ............................ 340/573.5 |
| 2007/0142799 A1 | 6/2007 | Ales et al. |
| 2008/0021423 A1 | 1/2008 | Klofta et al. |
| 2008/0054408 A1* | 3/2008 | Tippey et al. .................. 257/621 |
| 2008/0058745 A1 | 3/2008 | Long et al. |
| 2008/0168829 A1 | 7/2008 | Paez |
| 2008/0266122 A1* | 10/2008 | Ales et al. ...................... 340/604 |
| 2008/0287747 A1 | 11/2008 | Mestrovic et al. |
| 2009/0036850 A1* | 2/2009 | Nhan et al. ..................... 604/361 |
| 2010/0168694 A1 | 7/2010 | Gakhar et al. |
| 2010/0168702 A1 | 7/2010 | Ales, III et al. |
| 2010/0277324 A1 | 11/2010 | Yeh |
| 2012/0157947 A1* | 6/2012 | Nhan et al. ..................... 604/361 |

* cited by examiner

ATTACHMENT FOR A CONDUCTORLESS WETNESS DETECTOR FOR AN ABSORBENT ARTICLE

BACKGROUND

Absorbent articles such as diapers, training pants, incontinence products, feminine hygiene products, swim undergarments, and the like, conventionally include a liquid permeable body-side liner, a liquid impermeable outer cover, and an absorbent structure. The absorbent structure is typically located between the outer cover and the liner for taking in and retaining liquids (e.g., urine) exuded by the wearer. The absorbent structure can be made of, for instance, superabsorbent particles. Many absorbent articles, especially those sold under the trade name HUGGIES by the Kimberly-Clark Corporation, are so efficient at absorbing liquids that it is sometimes difficult to tell whether or not the absorbent article has been insulted with a body exudate, especially when the absorbent article is being worn by a newborn or other very young wearers. Insult amounts in such wearers tend to be very small. Other wearers might also produce very small insults.

Accordingly, various types of moisture or wetness indicators have been suggested for use in absorbent articles. The wetness indicators include various passive indicators such as indicator strips, printing, or other devices within each absorbent article, requiring a caregiver to pay for the wetness indicator in each absorbent article whether or not the caregiver intends to use the wetness indicator. Wetness indicators can also include alarm devices that are designed to assist parents or attendants in identifying a wet absorbent article condition early on. The devices can produce an audible, tactile, electromagnetic, or visual signal. Many of these devices rely on electronics, including conductive elements within each absorbent article that can increase the expense of the absorbent article.

In some aspects, for instance, conductive threads or foils have been placed in the absorbent articles that extend from the front of the article to the back of the article. The conductive materials serve as conductive leads for a signaling device and form an open circuit in the article that can be closed when a body fluid, such as urine, closes the circuit.

Incorporating conductive leads into absorbent articles, however, has caused various problems. For example, absorbent articles are typically mass produced on very fast moving machinery. Incorporating conductive leads into an absorbent article at conventional machine speeds has been problematic.

In addition, packaged absorbent articles are typically passed through a metal detector to ensure that there are no foreign objects contained in the package. If the conductive leads are made from or contain a metal, the metal detector can be activated registering a false positive. The incorporation of metallic materials into absorbent articles can also cause problems for those wearing the garments when attempting to pass through security gates that include metal detectors.

In view of the above, a need currently exists for a signaling system for an absorbent article that does not require conductive elements containing metal or other devices to be inserted into the interior of the article.

SUMMARY

The present inventors undertook intensive research and development efforts with respect to improving absorbent articles, particularly in providing a wetness indicator only when desired by a caregiver and without adding to the cost of an absorbent article. A need exists for wetness detection in absorbent articles and incontinence products in general. Technology that can be implemented without altering absorbent article construction is preferred.

The present disclosure is generally directed to various signaling systems that are particularly well suited for use in conjunction with absorbent articles. The signaling systems, for instance, can be connected to a signaling device that can be configured to emit a signal, such as an audible, tactile, electromagnetic or visual signal, for indicating to a user that a body fluid is present in the absorbent article. For example, in one aspect, the absorbent article includes a diaper and the signaling system is configured to indicate the presence of urine or a bowel movement. In other absorbent articles, however, the signaling systems can be configured to indicate the presence of yeast or metabolites.

More particularly, the present disclosure is directed to a wetness sensing system for use with an absorbent article having an outer surface, the system having a weight and including a holding fixture adapted to be attached to the outer surface of the absorbent article by a consumer, the holding fixture including a first attachment arm having an article-facing side including a first attachment material affixed thereto, and a sensor band including a sensor and having an article-facing side including a second attachment material affixed thereto, wherein the second attachment material has an area and is in a proportion of the area to the weight of the system of at least 0.2 sq. inch per gram, and wherein the sensor band has a bending stiffness of less than 30 gf cm^2/cm. The system also includes a signaling device coupled to the holding fixture and in electrical communication with the sensor, wherein the system is adapted to sense wetness within the article without the use of conductors within the absorbent article.

The present disclosure is also directed to a wetness sensing system for use with an absorbent article having an outer surface, the system having a weight and including a holding fixture adapted to be attached to the outer surface of the absorbent article by a consumer, the holding fixture having an article-facing surface and including an attachment arm and a sensor band including a sensor, wherein the article-facing surface is covered with an attachment material that has an area, is in a proportion of the area to the weight of the system of at least 0.2 sq. inch per gram, and demonstrates a peel force with respect to the outer surface of at least 11 gf/inch, and wherein the sensor band has a bending stiffness of less than 30 gf cm^2/cm. The system also includes a signaling device coupled to the holding fixture and in electrical communication with the sensor, wherein the system is adapted to sense wetness within the article without the use of conductors within the absorbent article.

The present disclosure is also directed to a wetness sensing system for use with an absorbent article having an outer surface, the system having a weight and including a holding fixture adapted to be attached to the outer surface of the absorbent article by a consumer, the holding fixture including an attachment arm having an article-facing side including a first attachment material affixed thereto, and a sensor band including a sensor and having an article-facing side including a second attachment material affixed thereto, wherein the second attachment material demonstrates a peel force with respect to the outer surface of at least 11 gf/inch; and wherein the sensor band has a bending stiffness of less than 30 gf cm^2/cm. The system also includes a signaling device coupled to the holding fixture and in electrical communication with the sensor, wherein the system is adapted to sense wetness within the article without the use of conductors within the absorbent article.

The present disclosure is also directed to a wetness sensing system for use with an absorbent article having an outer surface, the system having a weight and including a holding fixture adapted to be attached to the outer surface of the absorbent article by a consumer, the holding fixture including an attachment arm having an article-facing side including a first attachment material affixed thereto, and a sensor band including a sensor and having an article-facing side including a second attachment material affixed thereto, wherein the second attachment material has an area and is a microhook material that completely covers the article-facing side of the sensor band, demonstrates a peel force with respect to the outer surface of at least 11 gf/inch, and is in a proportion of the area to the weight of the system of at least 0.2 sq. inch per gram, and wherein the sensor band has a bending stiffness of less than 30 gf cm^2/cm. The system also includes a signaling device coupled to the holding fixture and in electrical communication with the sensor, wherein the system is adapted to sense wetness within the article without the use of conductors within the absorbent article.

Other features and aspects of the present disclosure are discussed in greater detail herein.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
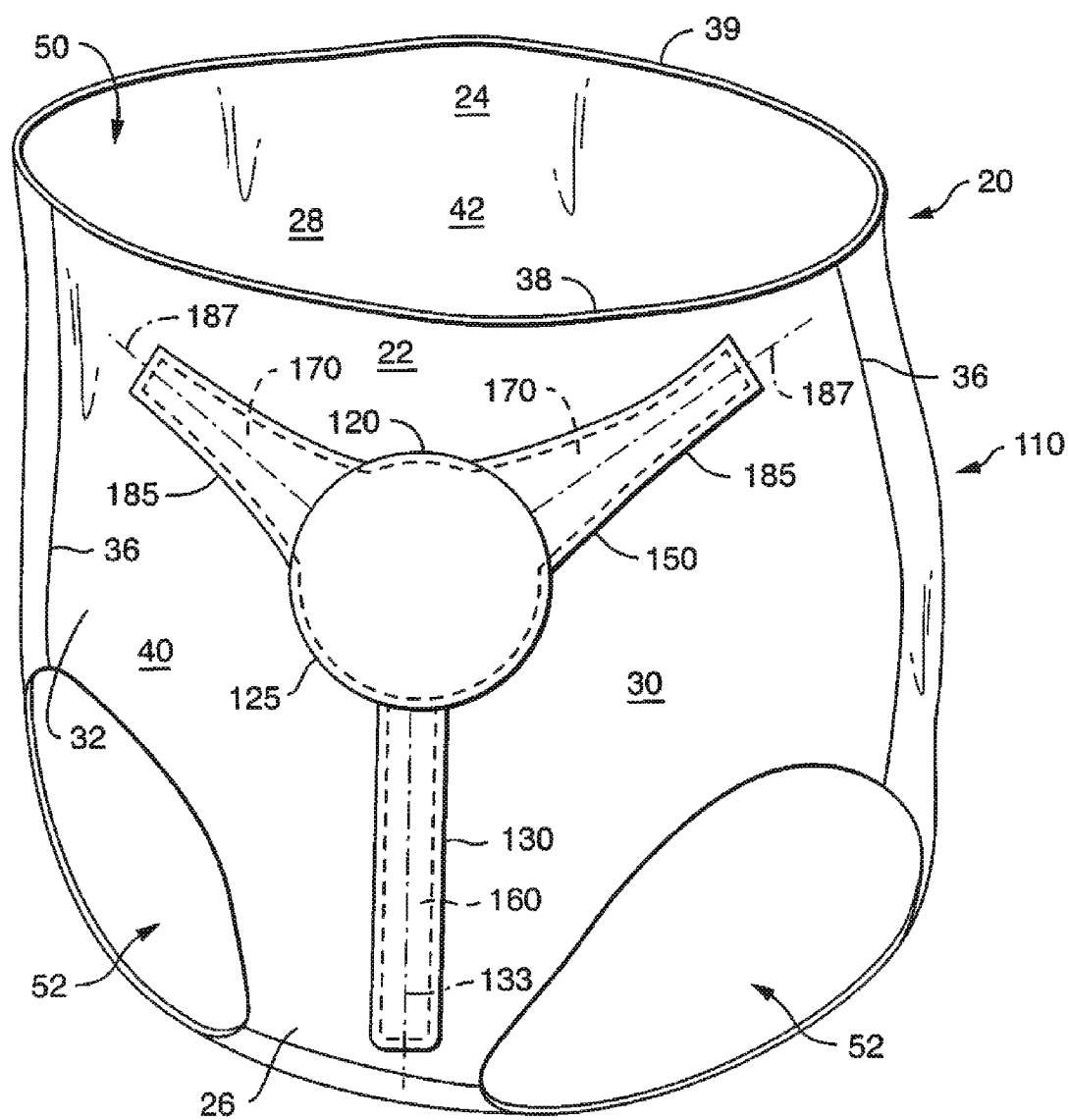
FIG. 1 is a front perspective view of an absorbent article including one aspect of a wetness detection system of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects only, and is not intended as limiting the broader aspects of the present disclosure.

The present disclosure is generally directed to signaling systems for absorbent articles that indicate to a user when a body fluid has insulted the article. For example, in one aspect, the signaling system is designed to emit a signal when urine is detected in the absorbent article. Of particular advantage, signaling systems made in accordance with the present disclosure can sense the presence of a body fluid within the absorbent article without having to construct the absorbent article with any elements or sensors contained in the interior of the article. In the past, for instance, metallic conductive leads were typically placed within the interior of the absorbent article. The signaling systems of the present disclosure, on the other hand, can sense the presence of a body fluid from an exterior surface of the article that can greatly simplify the incorporation of the signaling system into the article.

In accordance with the present disclosure, the signaling system can have various configurations and designs. Referring to FIG. 1, for exemplary purposes, an absorbent article 20 that can be used in conjunction with signaling systems of the present disclosure is shown. The absorbent article 20 can be disposable or not. It is understood that the present disclosure is suitable for use with various other absorbent articles intended for personal wear, including but not limited to diapers, training pants, swim pants, feminine hygiene products, incontinence products, medical garments, surgical pads and bandages, other personal care or health care garments, and the like, without departing from the scope of the present disclosure.

By way of illustration only, various materials and methods for constructing absorbent articles such as the absorbent article 20 of the various aspects of the present disclosure are disclosed in PCT Patent Application WO 00/037009 published Jun. 29, 2000 by A. Fletcher et al; U.S. Pat. No. 4,940,464 issued Jul. 10, 1990 to Van Compel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

An absorbent article 20 is representatively illustrated in FIG. 1. The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the absorbent article 20) to be disposed toward the wearer, and an outer surface 30 opposite the inner surface 28. The front and back regions 22, 24 are those portions of the absorbent article 20, that, when worn, wholly or partially cover or encircle the waist or mid-lower torso of the wearer. The crotch region 26 generally is that portion of the absorbent article 20 that, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32 that, in this aspect, encompasses the front region 22, the back region 24, and the crotch region 26. Referring to FIG. 1, the chassis 32 includes an outer cover 40 and a bodyside liner 42 that can be joined to the outer cover 40 in a superimposed relation therewith by adhesives, ultrasonic bonds, thermal bonds or other conventional techniques. The chassis 32 can further include an absorbent structure (not shown).

The absorbent article 20 can further include a pair of opposing elastic side panels (not shown) that are attached to the back region 24 of the chassis 32. The side panels can be stretched around the waist and/or hips of a wearer to secure the garment in place. In an alternative aspect, the elastic side panels can also be integrally formed with the chassis 32. For instance, the side panels can include an extension of the bodyside liner 42, of the outer cover 40, or of both the bodyside liner 42 and the outer cover 40. It should be understood, however, that the side panels can alternatively be connected to the front region 22 of the article 20.

The elastic side panels can be connected by a fastening system (not shown) to define a three-dimensional absorbent article configuration having a waist opening 50 and a pair of leg openings 52. The waist opening 50 of the absorbent article 20 is defined by the waist edges 38 and 39 that encircle the waist of the wearer.

The side panels can be releasably attachable to the front region 22 of the article 20 by the fastening system. In other aspects, the side panels can be permanently joined to the chassis 32 at each end. The side panels can be permanently bonded together, for instance, when forming a training pant or absorbent swimwear.

In addition to possibly having elastic side panels, the absorbent article 20 can include various waist elastic members (not shown) for providing elasticity around the waist opening 50.

The absorbent article 20 can include a wetness sensing system 110 that can be used to detect wetness, such as from urine, feces, or other body exudates, within the absorbent article 20. The wetness sensing system 110 includes a reusable signaling device 120 and a holding fixture 150.

The reusable signaling device 120 is adapted to sense wetness without the use of conductors within the absorbent article 20. Suitable wetness sensing technologies include capacitance-based sensors such as those described in co-pending U.S. patent application Ser. No. 12/648,645, inductance-based sensors such as those described in co-pending U.S. patent application Ser. No. 11/983,970, and infrared reflectance-based sensors such as those described in co-pending U.S. patent application Ser. No. 12/636,888, each of which is incorporated herein by reference to the extent it does not conflict herewith. Any other suitable sensor technology can be employed.

Sensors such as those described herein are further described, for instance, in U.S. Patent Application Publication No. 2008/0048786, which is incorporated herein by reference to the extent it does not conflict herewith.

The signaling device 120 can include a housing 125. The housing 125 can be designed so that the signaling device 120 minimizes any discomfort when worn. In addition to being comfortable when attached to an absorbent article 20, however, the signaling device 120 must also be durable. Based upon anthropomorphic modeling, signaling devices 120 made in accordance with the present disclosure are produced with dimensions that fall within a set of desirable ranges. In addition, the signaling device 120 can also include radii on the corners of the signaling device 120 that are constrained by a set of desirable ranges to ensure that the corners do not impinge, scratch, or poke the body's surface.

In this aspect, the signaling device 120 can include a housing 125 that contains the internal components. The internal components, for instance, can include a battery and can be configured to generate an audible signal, a tactile signal, an electromagnetic signal, a wireless signal, a visual signal, any other suitable signal, or any combination of these. The housing 125 in this aspect can have a rectangular shape, such as a square shape, with rounded corners, or the housing 125 can be circular, ovoid, or any other suitable shape. Housings 125 suitable for use in the wetness sensing system 110 described herein include those further described, for instance, in U.S. patent application Ser. No. 11/848,714, which is incorporated herein by reference to the extent it does not conflict herewith.

As illustrated in FIG. 1, the signaling device 120 can also include a flexible sensor band 130 extending from the housing 125. In a particular aspect of the present application, the flexible sensor band 130 is a flexible plastic film including an array of capacitive-based sensing elements. The sensing elements can take form of two planar electrodes making an open-face virtual capacitor. The flexible sensor band 130 can be made by etching from copper sheets laminated onto a flexible and non-conductive substrate. Such flexible and non-conductive substrates include polyimide, polyester, and any other suitable material. An example of such material is KAPTON film made by E. I. du Pont de Nemours and Company of Wilmington, Del., U.S.A. The etching method is widely used to make printed circuit boards in the electronic industry.

Other methods of making a flexible printed circuit board include silk screen printing, gravure printing, and flexographic printing. The conductive material forming open face capacitors is made with conductive materials such as copper, silver, or carbon black. The flexible sensor band 130 can be electrically connected to the signaling device 120 by a ZIF connector or any other suitable connector.

With respect to the specific example described herein, recent research has discovered that an inconsistent or excessive distance between a capacitive-based sensing element and a substance being detected can alter or eliminate the sensing function, leading to inaccurate results. The wearer's movement can create or enhance inconsistencies in distances. As a result, capacitive-based sensing elements benefit from and can even require secure attachment over the complete sensing area because capacitance is sensitive to distance and/or depth.

In addition, a sensor band 130 that is too long or too short can also adversely impact the sensing functionality of the signaling device 120 because the signaling device will not be properly sized to accommodate movement and/or to cover the region of interest. The sensor band 130 can be of any shape including linear, arcuate, circular, or irregular, including having a widened portion at one end of the sensor band 130.

Oil such as mineral oil can be inherent in standard materials used in such applications. Oil can adversely impact the ability of the signaling device 120 to remain sufficiently attached to the outer surface 30 because such mineral oil impedes the ability of attachment mechanisms to remain attached to the signaling device 120. Some polymers otherwise suitable for such an application include mineral oil to make portions of the signaling device 120 flexible. In one example, the amount of mineral oil can be reduced by selecting particular polymers as are known to those skilled in the art.

In one aspect of the present invention, the entire article-facing surface of the sensor band 130 can include the capacity to be attached to the outer surface 30 of the absorbent article 20. In another aspect, substantially all of the article-facing surface of the sensor band 130 can include the capacity to be attached to the outer surface 30 of the absorbent article 20. In another aspect, a majority of the article-facing surface of the sensor band 130 can include the capacity to be attached to the outer surface 30 of the absorbent article 20. In another aspect, half of the article-facing surface of the sensor band 130 can include the capacity to be attached to the outer surface 30 of the absorbent article 20. Finally, in another aspect, a portion of the article-facing surface of the sensor band 130 can include the capacity to be attached to the outer surface 30 of the absorbent article 20.

The flexible sensor band 130 can include an attachment material 160 such that the flexible sensor band 130 is attachable to the outer surface 30 of the absorbent article 20 by the consumer. The flexible sensor band 130 can be attachable to the outer surface 30 using adhesives, cohesives, mechanical fasteners such as hook material, or any other suitable attachment material.

As stated above, the wetness sensing system 110 includes a holding fixture 150. The signaling device 120 is attached to the holding fixture 150 by either a manufacturer or by a consumer. The holding fixture 150 can be part of the signaling device 120 when the signaling device 120 is made. In other aspects, the holding fixture 150 can be attached to the signaling device 120 by injection molding, stitching, adhesive bonding, ultrasonic bonding or thermal bonding. The holding fixture 150 can also be attached to the signaling device 120 by a mechanical attachment means, such as nut and bolt, snap-on or screw-on configurations, or any other suitable attachment material.

The holding fixture 150 is adapted to be attached to the outer surface 30 of the absorbent article 20, particularly by a consumer. The holding fixture 150 is attached to the outer surface 30 such that the signaling device 120 is positioned adjacent the outer surface 30 of the absorbent article 20. Depending on the manufacturing process, the sensor band 130 can be considered part of the signaling device 120 or part of the holding fixture 150.

The wetness sensing system 110 is preferably sized and positioned such that the sensor band 130 is disposed adjacent to the region of the absorbent article 20 most likely to receive an insult of interest. In a specific aspect, the flexible sensor band 130 should be long enough to cover at least a quarter of the length of the absorbent article 20, from the midpoint of the absorbent article 20 toward the front of the absorbent article 20. It should be noted that regions of interest can vary by product type, product size, and by the gender of the intended wearer.

In an aspect of the present disclosure illustrated in FIG. 1, the holding fixture 150 includes flexible arms 185. The flexible arms 185 are attachable to the outer surface 30 by the consumer. The holding fixture 150 and/or the flexible arms 185 can be attachable to the outer surface 30 using adhesives, cohesives, mechanical fasteners such as hook material, or any other suitable attachment material 170.

In a particular aspect of the present application, the holding fixture 150 including the flexible arms 185 can be formed integrally with the sensor band 130, with the signaling device 120, or with both. The flexible arms 185 can be of any shape including linear, arcuate, circular, or irregular, including having a widened portion at one end of the flexible arms 185.

In a particular aspect of the present application, the attachment material 170 is primarily hook material bonded to the holding fixture 150 such that the hooks of the hook material can engage with the outer surface 30. Hook specifications are important to the success of the attachment of the holding fixture 150 to the outer surface 30. Hook that is too tall can place the sensor band 130 too far from the outer surface 30. Hook that is too small can be more skin-friendly but might not effectively engage the outer surface 30.

The signaling device 120 should remain in place and conform to the absorbent article 20 and the body of the wearer for proper functionality. To this end, at least a portion of the holding fixture 150 including the attachment material 170 such as hook material and the adhesive used to bond the hook material to the holding fixture 150 should be flexible. Flexibility in this aspect is measured in the form of bending stiffness as determined using a bending stiffness tester, in this case Model KES-FB2-L in association with its data acquisition unit and program KES-FB System Measurement Program FB2-L Only Ver. 7.09 WJ For Win 98, NT, 2000, made by Kato Tech Co., Ltd. in Japan. In various aspects, the bending stiffness should be less than 100 gf cm^2/cm, less than 75 gf cm^2/cm, less than 50 gf cm^2/cm, less than 35 gf cm^2/cm, less than 30 gf cm^2/cm, or less than 25 gf cm^2/cm.

Table 1 identifies the results of bending stiffness testing on various materials and material combinations that might be used in the present device.

TABLE 1

Bending stiffness

| Material | Manufacturer | Bending Stiffness (gf cm$^2$/cm) |
|---|---|---|
| Sensor (CY081-B casing + 97-3257 Hook + Polyester capacitive sensor Strip) | | 29.62 |
| Dynaflex 7930A casing | PolyOne Corp., McHenry, IL, U.S.A. | 24.70 |
| Dynaflex G-7950 casing | PolyOne Corp., McHenry, IL, U.S.A. | 54.5 |
| Dynalloy 8900-30 | PolyOne Corp., McHenry, IL, U.S.A. | 22.38 |
| Polyimide 2 mil capacitive sensor strip with etched copper traces | Plexus, Neenah, WI, U.S.A. | 60.30 |
| Polyimide 4 mil capacitive sensor strip with etched copper traces | Plexus, Neenah, WI, U.S.A. | 127.9 |
| Polyester capacitive sensor Strip with Silver printed traces | Soligie, Inc., Savage, MN, U.S.A. | 9.62 |
| 97-3257 Hook Material | Velcro USA Inc., Manchester, NH, U.S.A. | 1.47 |

CY081-B casing:
80% Kraton G1645 (from Kraton Polymers) + 20% ESCORENE EVA 7710 (from Exxon Mobil Corporation)

In one aspect of the present application, the signaling device 120 can advantageously include a rigid portion in addition to the flexible portion. Such a rigid portion can include an electronic circuit board, a battery, and any other necessary or desired components. In other aspects, the use of flexible components can eliminate the need for a rigid portion.

In addition, for the aspects in which hook material is used as the attachment material 160 and/or 170, the hook material should have a hook-area-to-sensor-weight ratio of at least 0.1 sq. inch per gram, at least 0.2 sq. inch per gram, at least 0.25 sq. inch per gram, or at least 0.3 sq. inch per gram. Data shown in Table 2 were obtained from a use study.

TABLE 2

| Description | Hook area (sq inch) | Sensor Weight (g) | Hook area/ sensor weight (inch$^2$/g) | % "sensor head" detached in use |
|---|---|---|---|---|
| Small wings | 8.98 | 37 | 0.24 | 10.5 |
| Medium wings | 11.65 | 34 | 0.34 | 7.1 |
| Large wings | 14.32 | 40 | 0.36 | 0.0 |

Further, for the aspects in which hook material is used as the attachment material 160 and/or 170, the hook material should have a peel strength with respect to the outer surface 30 of at least 5 gf/inch (0.2 gf/mm), of at least 11 gf/inch (0.4 gf/mm), of at least 25 gf/inch (1.0 gf/mm), of a least 40 gf/inch (1.6 gf/mm), of at least 60 gf/inch (2.4 gf/mm), or of at least 90 gf/inch (3.5 gf/mm). The peel strength of the hook material was measured using a CRE (Constant Rate of Extension) tensile tester with a computer-based data acquisition and frame control system such as MTS TestWorks® for Windows software version 4.0 from MTS Systems Corporation, Eden Prairie, Minn., or Instron Bluehill 2 from Instron Corporation, Norwood, Mass., or equivalent.

The gauge length was set at 1.5±0.04 inches (38±1 mm) with test speed of 40±0.04 inches (1016±10 mm) per minute. A piece of hook sample of 1.5 inches (38 mm) wide×4 inches (101 mm) long was engaged to a piece of outer cover material that was 2 inches (50 mm) wide×4 inches (101 mm) long using a roller with weight of 2 kg. The hook sample was placed in the top grip and the outer cover sample in the bottom grip of the tensile tester. The peel distance was set at 4 inches (101 mm). The average peel force was calculated between 1 inch (25 mm) and 3 inches (76 mm) of peel distance and then used to calculate the average peel force over 1.5 inches (38 mm) of hook sample width with the final unit of gf/in.

Figure 2:
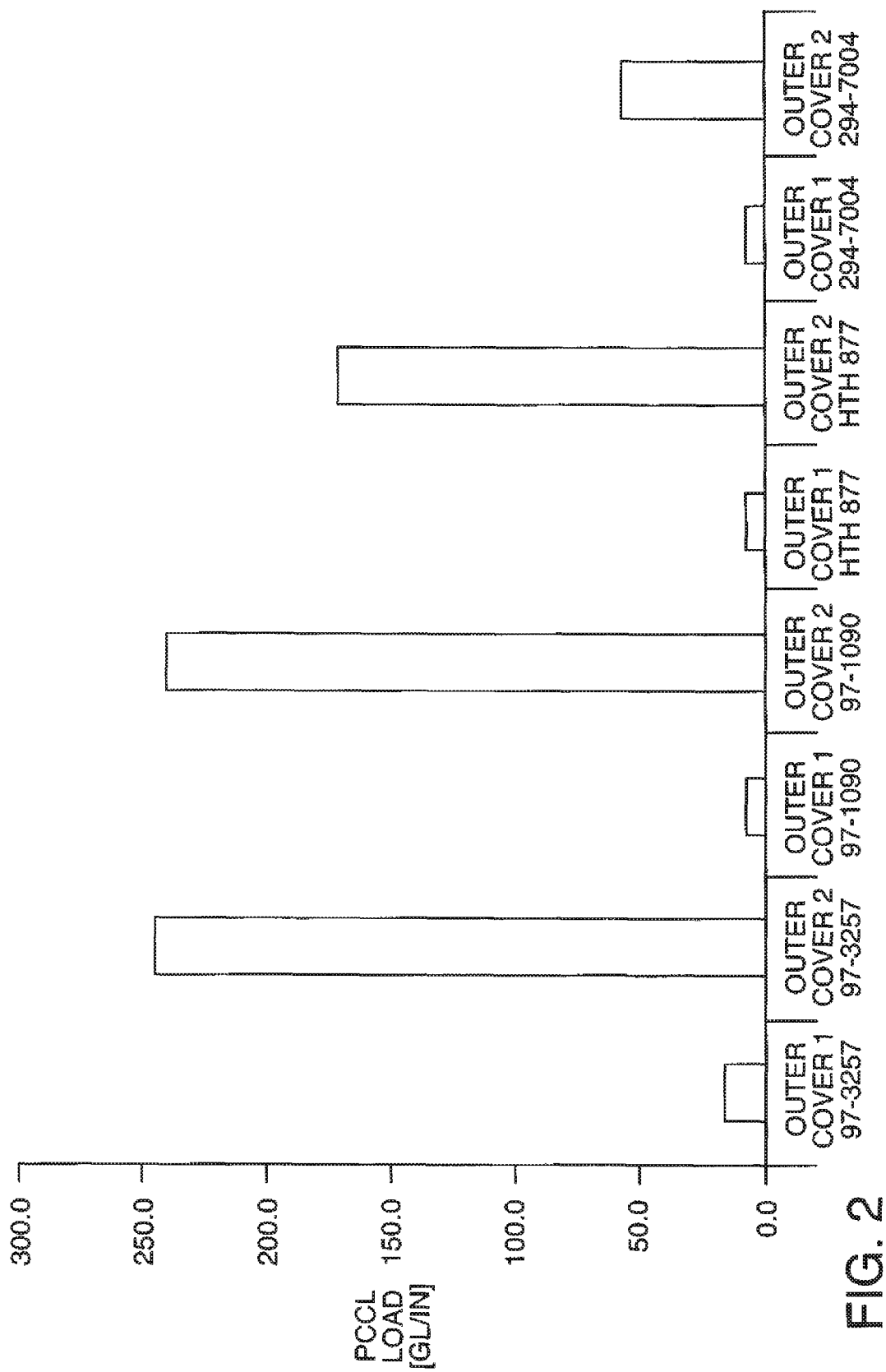
FIG. 2 is a graphical representation of peel strength testing results of materials potentially usable with the wetness detection system of FIG. 1.

FIG. 2 and Table 3 illustrate the average peel strength of different hook materials attaching to two different outercover materials. Materials 97-3257, 97-1090, HTH 877 and 294-7004 are hook materials available from Velcro USA. Outercover 1 is a polyethylene film laminated to 20 gsm spunbond available from Kimberly-Clark Corporation located in Dallas, Tex., U.S.A. Outercover 2 is a polyethylene film laminated to 14 gsm bico spunbond available from Avgol American Inc. located in Mocksville, N.C., U.S.A.

TABLE 3

| ID | Avg Peel (gf/in) | Avg Peel (gf/mm) |
|---|---|---|
| 97-3257 w/aSFL | 10.6 | 0.4 |
| 97-3257 w/BICO | 164.0 | 6.5 |
| 97-1090 w/aSFL | 5.1 | 0.2 |
| 97-1090 w/BICO | 160.7 | 6.3 |
| 877 w/aSFL | 5.6 | 0.2 |
| 877 w/BICO | 114.9 | 4.5 |
| 732 w/aSFL | 3.9 | 0.2 |
| 732 w/BICO | 95.2 | 3.8 |
| 294-1001 w/aSFL | 11.0 | 0.4 |
| 294-1001 w/BICO | 33.3 | 1.3 |
| 294-7004 w/aSFL | 5.0 | 0.2 |
| 294-7004 w/BICO | 38.8 | 1.5 |
| 97-3257 w/3905 | 34.9 | 1.4 |
| 97-3257 w/FNL 251 | 1272.6 | 50.2 |
| 732 w/3905 | 131.3 | 5.2 |
| 732 w/FNL 251 | 983.8 | 38.8 |

Each flexible arm 185 has a flexible arm centerline 187. The flexible sensor band 130 has a sensor band centerline 133. One or both of the flexible arms 185 can extend from the center of the holding fixture 150 such that a flexible arm centerline 187 is at an obtuse angle to the sensor band centerline 133 to provide additional support to keep the holding fixture 150 attached to the outer surface 30 of the absorbent article 20. In a particular aspect, the flexible arm centerlines 187 with the sensor band centerline 133 form a Y-shape, as illustrated in FIG. 1.

In one aspect of the present application, the entire article-facing surfaces of the holding fixture 150 and/or the flexible arms 185 can include the capacity to be attached to the outer surface 30 of the absorbent article 20. In another aspect, substantially all of the article-facing surface of the holding fixture 150 and/or the flexible arms 185 can include the capacity to be attached to the outer surface 30 of the absorbent article 20. In another aspect, a majority of the article-facing surface of the holding fixture 150 and/or the flexible arms 185 can include the capacity to be attached to the outer surface 30 of the absorbent article 20. In another aspect, half of the article-facing surface of the holding fixture 150 and/or the flexible arms 185 can include the capacity to be attached to the outer surface 30 of the absorbent article 20. Finally, in another aspect, a portion of the article-facing surface of the holding fixture 150 and/or the flexible arms 185 can include the capacity to be attached to the outer surface 30 of the absorbent article 20.

In some aspects, once the consumer attaches the flexible arms 185 and the flexible sensor band 130 to the outer surface 30, the consumer can then attach the signaling device 120 to the holding fixture 150. In other aspects, the signaling device 120 is attached to the holding fixture 150 by a manufacturer, and the consumer only needs to attach the holding fixture 150 to the outer surface 30. The signaling device 120 is then ready to sense wetness within the absorbent article 20. The flexible arms 185 and the flexible sensor band 130 can be manufactured from woven material or non-woven material such as SMS, spun-bond, film such as polypropylene, rubber, other elastomeric material, or from any other suitable material, either alone or laminated to a non-woven.

In an alternate aspect of the present disclosure, the flexible arms 185, the flexible band 130, and the signaling device 120 can be formed together as one unit of injection-molded plastic or other suitable material. The attachment material 160, 170 can be an adhesive, a cohesive, hook material, or any other suitable attachment material.

Various attachment mechanisms include those disclosed in co-pending and co-assigned U.S. Patent Application Publication No. 2007/0142797 to Long, et al. and entitled "Garments With Easy-To-Use Signaling Device"; U.S. Patent Application Publication No. 2006/0244614 to Long and entitled "Connection Mechanisms"; and U.S. Patent Application Publication No. 2007/0024457 to Long, et al. and entitled "Connection Mechanisms In Absorbent Articles For Body Fluid Signaling Devices," which are incorporated herein by reference to the extent they are consistent (i.e., not in conflict) herewith.

The holding fixture 150 can be designed to be disposable with the article 20 to which it is attached if generally disposable materials are chosen for the holding fixture 150. Providing a holding fixture 150 that is disposable with the article 20 can provide improved cleanliness, and ease of use, and can benefit from not needing to be removed from a used article 20. A holding fixture 150 might also not be easy to reattach if used more than once. In these aspects the materials from which the holding fixture 150 is made from should be relatively inexpensive.

The holding fixture 150 can be designed for reuse if generally durable materials are chosen for the holding fixture 150. Providing a reusable holding fixture 150 enhances durability, is more easily washed, and its positioning can be more easily adjusted if a mechanical fastener such as hook material is used instead of an adhesive.

The signaling device 120 can emit any suitable signal to indicate to the user that the absorbent article 20 has been insulted. The signal, for instance, can include an audible signal, a tactile signal, an electromagnetic signal, a wireless signal, a visual signal, any other suitable signal, or any combination of these. The audible signal, for instance, can be as simple as a beep or can include a musical tune. In still another aspect, the signaling device can emit a wireless signal that then activates a remote device, such as a telephone or a pager.

Further aspects of the signaling device 120 can be found in co-pending U.S. patent application Ser. No. 12/347,539, entitled "Remote Detection Systems For Absorbent Articles," which is incorporated herein by reference to the extent it does not conflict herewith.

In an alternative aspect, the signaling device 120 can be configured to be removed from the absorbent article 20 to be disposed of and placed on a new absorbent article 20. In fact, in one aspect, the signaling device 120 can include multiple settings depending upon the absorbent article 20 to which it is attached. In this manner, the signaling system can be modified based upon the particular product specifications. The product purchased can provide information to the consumer as to which setting to use.

These and other modifications and variations to the present disclosure can be practiced by those of ordinary skill in the art, without departing from the spirit and scope of the present disclosure, which is more particularly set forth in the appended claims. In addition, it should be understood that elements of the various aspects can be interchanged both in whole and in part. Furthermore, those of ordinary skill in the art will appreciate that the foregoing description is by way of example only, and is not intended to limit the disclosure so further described in such appended claims.

What is claimed:

1. A wetness sensing system for use with an absorbent article having an outer surface, the system having a weight and comprising:
    a holding fixture adapted to be attached to the outer surface of the absorbent article by a consumer, the holding fixture including
        a first attachment arm having an article-facing side including a first attachment material affixed thereto, and
        a sensor band including a sensor and having an article-facing side including a second attachment material affixed thereto, wherein the second attachment material has an area and is in a proportion of the area to the weight of the system of at least 0.2 sq. inch per gram, and wherein the sensor band has a bending stiffness of less than 30 gf cm^2/cm; and
    a signaling device coupled to the holding fixture and in electrical communication with the sensor, wherein the system is adapted to sense wetness within the article without the use of conductors within the absorbent article.

2. The system of claim 1, wherein the second attachment material is a microhook material.

3. The system of claim 1, wherein the second attachment material completely covers the article-facing side of the sensor band.

4. The system of claim 1, wherein the first attachment material completely covers the article-facing side of the first attachment arm.

5. The system of claim 1, wherein the second attachment material demonstrates a peel force with respect to the outer surface of at least 11 gf/inch.

6. The system of claim 1, wherein the first attachment material is the same material as the second attachment material.

7. The system of claim 1, further comprising a second attachment arm having an article-facing side including the first attachment material affixed thereto.

8. The system of claim 7, wherein each attachment arm has an attachment arm centerline, the sensor band has a sensor band centerline, and wherein each attachment arm centerline is at an obtuse angle to the sensor band centerline.

9. The system of claim 8, wherein the sensor band centerline and the attachment arm centerlines form a Y shape.

10. The system of claim 1, wherein the attachment arm has an attachment arm centerline, the sensor band has a sensor band centerline, and wherein the attachment arm centerline is at an obtuse angle to the sensor band centerline.

11. The system of claim 1, wherein the signaling device is formed integrally with the holding fixture.

12. A wetness sensing system for use with an absorbent article having an outer surface, the system having a weight and comprising:
    a holding fixture adapted to be attached to the outer surface of the absorbent article by a consumer, the holding fixture having an article-facing surface and including an attachment arm and a sensor band including a sensor, wherein the article-facing surface is covered with an attachment material that has an area, is in a proportion of the area to the weight of the system of at least 0.2 sq. inch per gram, and demonstrates a peel force with respect to the outer surface of at least 11 gf/inch, and wherein the sensor band has a bending stiffness of less than 30 gf cm^2/cm; and
    a signaling device coupled to the holding fixture and in electrical communication with the sensor, wherein the system is adapted to sense wetness within the article without the use of conductors within the absorbent article.

13. A wetness sensing system for use with an absorbent article having an outer surface, the system having a weight and comprising:
    a holding fixture adapted to be attached to the outer surface of the absorbent article by a consumer, the holding fixture including
        an attachment arm having an article-facing side including a first attachment material affixed thereto, and
        a sensor band including a sensor and having an article-facing side including a second attachment material affixed thereto, wherein the second attachment material demonstrates a peel force with respect to the outer surface of at least 11 gf/inch; and wherein the sensor band has a bending stiffness of less than 30 gf cm^2/cm; and
    a signaling device coupled to the holding fixture and in electrical communication with the sensor, wherein the system is adapted to sense wetness within the article without the use of conductors within the absorbent article.

14. The system of claim 13, wherein the second attachment material has an area and is in a proportion of the area to the weight of the system of at least 0.2 sq. inch per gram.

15. The system of claim 13, wherein the second attachment material completely covers the article-facing side of the sensor band.

16. The system of claim 13, wherein the first attachment material completely covers the article-facing side of the attachment arm.

17. A wetness sensing system for use with an absorbent article having an outer surface, the system having a weight and comprising:
    a holding fixture adapted to be attached to the outer surface of the absorbent article by a consumer, the holding fixture including
        an attachment arm having an article-facing side including a first attachment material affixed thereto, and
        a sensor band including a sensor and having an article-facing side including a second attachment material affixed thereto, wherein the second attachment material has an area and is a microhook material that completely covers the article-facing side of the sensor band, demonstrates a peel force with respect to the outer surface of at least 11 gf/inch, and is in a proportion of the area to the weight of the system of at least 0.2 sq. inch per gram, and wherein the sensor band has a bending stiffness of less than 30 gf cm^2/cm; and a signaling device coupled to the holding fixture and in electrical communication with the sensor, wherein the system is adapted to sense wetness within the article without the use of conductors within the absorbent article.

18. The system of claim 17, wherein the first attachment material is the same material as the second attachment material.

19. The system of claim 17, wherein the second attachment material completely covers the article-facing side of the sensor band.

20. The system of claim 17, wherein the first attachment material completely covers the article-facing side of the first attachment arm.

* * * * *